United States Patent
Larsen

(10) Patent No.: US 6,492,135 B1
(45) Date of Patent: Dec. 10, 2002

(54) U-SHAPE AND/OR NOZZLE U-LOOP FERMENTOR AND METHOD OF CARRYING OUT A FERMENTATION PROCESS

(76) Inventor: Ebbe Busch Larsen, C/O UniBio Tech A/s, Nørregade 73, 1.th., DK-5000, Odense C (DK)

( * ) Notice: Subject to any disclaimer, the term of this patent is extended or adjusted under 35 U.S.C. 154(b) by 0 days.

(21) Appl. No.: 09/979,574

(22) PCT Filed: May 18, 2000

(86) PCT No.: PCT/DK00/00269

§ 371 (c)(1),
(2), (4) Date: Feb. 28, 2002

(87) PCT Pub. No.: WO00/70014

PCT Pub. Date: Nov. 23, 2000

(30) Foreign Application Priority Data

May 18, 1999 (DK) .................... 1999 00690

(51) Int. Cl.[7] .................. C12P 1/00
(52) U.S. Cl. ........... 435/41; 435/293.1; 435/295.2; 435/813
(58) Field of Search ............ 435/293.1, 295.2, 435/873, 41

(56) References Cited

U.S. PATENT DOCUMENTS 4,116,977 A * 9/1978 Yamabe et al. ............ 549/266
5,073,496 A * 12/1991 Oosterhuis et al. ......... 422/132
5,342,781 A * 8/1994 Su .............................. 210/194

FOREIGN PATENT DOCUMENTS

EP 0418187 A1 * 3/1991

* cited by examiner

Primary Examiner—David A. Redding
(74) Attorney, Agent, or Firm—William J. Sapone; Coleman Sudol Sapone, P.C.

(57) ABSTRACT

A U-shape and/or nozzle-U-loop fermentor has a U-part consisting of an essentially vertical downstream part (2), an essentially vertical upstream part (4), a U-shape bend part (3) which connects the lower ends of the downstream and upstream parts, an inline pump (12) placed in the U-part for circulation of fermentation liquid in the fermentor, a top part (5) which is placed above the upper end of the downstream part, gas supply members (7, 8, 9, 10) which are provided in the U-part with appending static-mechanical mixing members (13, 14, 15, 16, 17) for the comminution of the gases introduced into the fermentation liquid, and supply numbers for water and nutrient salts (18) and (19), respectively, and in connection with the supply members (7, 8, 9, 10, 18, 19) or in by-pass arrangements in connection therewith one (or more) ion sensor(s) or analyser(s) (20, 21, 22, 23) for sensing the concentration of at least one of the ion species phosphate, ammonium, nitrate and hydrogen ion, oxygen sensor(s) for sensing the oxygen concentration, and at least one thermo phial for sensing the temperature, said sensor(s), analyser(s) and phial(s) delivering signals to a data processing system (PC), wherein the signals received are processed and the dosage of feed gases, water, minerals and pH adjustment means via the supply members (7, 8, 9, 10, 18, 19) are calculated and optimised from pre-programmed amounts relative to the results measured.

9 Claims, 1 Drawing Sheet

U-SHAPE AND/OR NOZZLE U-LOOP FERMENTOR AND METHOD OF CARRYING OUT A FERMENTATION PROCESS

FIELD OF THE INVENTION

In its broadest aspect the present invention relates to U-shape and/or nozzle-U-loop fermentors and methods of the operation of the same.

More specifically the invention relates to U-shape and/or nozzle-U-loop fermentors and methods for the operation of the same, which are particularly appropriate for production processes with methanotrophic bacteria and similar processes, whereby different gases and other nutrients are to be supplied to the fermentation liquid in order to obtain an optimally proceeding fermentation process with the highest possible yield of fermentation product in the shortest possible period of time.

PRIOR ART

Stirred Or Back-mix Fermentors

In conventional bioreactors (fermentors) the mixing of gases with the fermentation liquid is effected by means of stirrer blades placed centrally in the fermentor. The stirrer blades generate turbulence in the liquid, which means that gas, usually injected at the bottom of the reactor, will be dissipated in the liquid in the form of small fine gas bubbles. This type of reactor provides a relatively homogenous mixing, i.e. that about the same concentrations of gases and substrates will be found whether measuring at the top or at the bottom of the reactor. This type of reactor is, however, not particularly appropriate for up-scaling, since it is difficult to obtain the same homogeneous mixing and the same mass transportation in large reactors as can be obtained in small laboratory and pilot reactors. Besides, the vigorous mixing implies a significant heating of the fermentation liquid.

Airlift and Loop Fermentors

In order to avoid the mechanical stirring, different types of airlift reactors have been developed. The majority of these reactors are so-called loop reactors having two sections: an upstream part and a downstream part, which are interconnected at both ends. Gases are supplied at the bottom of the reactor in the upstream part in an arrangement, which yields small gas bubbles (e.g. through a vitrified ceramic plate or an array of small nozzles). The bubbles mix with the liquid whereby the total density is reduced and the gas-liquid mixture ascends displaced by new liquid emerging from the downstream part. The gas-liquid mixture moves up through the upstream part of the reactor and releases its gas bubbles at the top, whereupon the liquid descends down through the downstream part. In order to obtain a long residence time for the gas bubbles in the liquid, airlift reactors are conventionally tall slender reactors. This implies that the gas must be supplied at a high pressure for overcoming the hydrostatic pressure at the bottom of the reactor. If the gas is air, this implies the use of compressors. Furthermore, airlift reactors have a relatively poor exploitation of the injected gas. Typically only 20–40% of the gas is utilized. Besides, it is difficult to obtain good and quick release of the gas bubbles from the fermentation liquid at the top of the reactor and separation of the gas phase thus produced (which may be rather foaming) from the liquid phase before the fermentation liquid moves down in the downstream part of the reactor.

U-shape Reactor

The U-shape reactor is constructed with a view to provide:

Non-compressed or nearly non-compressed gas injection
Long residence time and thus high degree of exploitation of the injected gas
Low energy consumption for liquid circulation
Simple design
Good separation of gases and liquid at the top.

In principle the U-shape reactor is also a loop reactor. However, contradictory to conventional loop reactors the liquid circulation is effected by means of one or more in-line pumps. This (or these) pump(s) may be of the propeller pump type, wherein the propeller blades are designed for pumping a mixture of liquid and gas. The gases can be introduced at different locations in the U-shape loop, but typically they will be supplied at the upper end of the downstream part of the loop. By introducing the gases at the upper end of the downstream part of the loop a nearly non-compressed injection is obtained, since the gases only have to overcome a hydrostatic pressure of some few meters. The gases can be introduced by means of particular gas dispensers providing for a distribution across the downstream part of the loop. Fine dispersion of the gases in the liquid is effected by means of static mixing elements placed immediate below the gas injectors (the mixing elements may be of e.g. Sulzer manufacture). The liquid flow in the downstream part of the loop must be sufficiently high so that all the injected gas is carried along down through the static mixers. Here a comminution of the gas is effected so that a large number of small gas bubbles is obtained, which are dispersed uniformly in the liquid. The bubbles are carried along with the liquid flow down through the downstream part of the loop to its lower end and further on through a U-bend to the upstream part of the loop so that the gas bubbles are redispersed (e.g. by means of static mixing elements) several times in the liquid.

The U-bend causes a centrifugal effect and thus some separation of gas bubbles and liquid.

Therefore, the in-line pump is preferably placed adjacent the U-bend, partially because it then assists in producing a redispersing of the gas in the liquid and partially because it is practical to have it placed at the bottom of the fermentor.

In order to obtain a good bubble distribution in the upstream part of the loop more static mixers may be provided therein.

The top of the fermentor is designed so that the upstream part of the loop via a bend is passed horizontally onto the side of a widening of the upper end of the downstream part of the loop. This particular construction feature assists in yielding a good separation of liquid and gas bubbles, as centrifugal forces act in the bend and in the very widening of the upper end of the downstream part of the loop a vigorous circulation of the liquid with corresponding accompanying centrifugal forces arise, which also bring about separation of liquid and gas bubbles. Thereby, one of the great problems associated with airlift reactors—viz. separation of the gas and liquid phases—is solved in an utmost elegant fashion.

Furthermore, the U-shape reactor provides for a long contact time between the gas and liquid phases, as the injected gas is present both in the downstream and in the upstream parts of the loop. This means that an essentially higher utilization of the gas is obtained compared with conventional airlift reactors.

Gas bubbles in liquids have a tendency to fuse together to larger volumes (coalesce). This tendency contributes to making conventional airlift reactors ineffective inasmuch as the bubbles become larger and larger upward through the upstream part, partly due to coalescence and partly due to a reduced hydrostatic pressure. In the U-shape reactor here described, this tendency in the upstream part is counteracted by providing static mixers appropriately spaced apart at distances, which depend on the medium applied. In the downstream part, the increasing hydrostatic pressure counteracts the tendency to increased bubble sizes. To the extent that this effect cannot balance the fusion (coalescence) of the gas bubbles there is provided for a redispersing by means of static mixers.

The amount of gas, which advantageously can be dispersed in the liquid, depends on the hydrostatic pressure. In the case of tall reactors it will therefore be advantageous to have several locations for the introduction of gases in the downstream part. The only requirement to the gas inlets is that at least one static mixing element is placed immediately after each inlet for dispersing the gas in the liquid.

In order to give an impression of the dimensions, which such a U-shape reactor may have it may be mentioned that its total height can be about 40 metres and its width can be about 6.6 metres, the said width is to be understood as the perpendicular distance between the portions of the vertical walls of the downstream and upstream parts being spaced furthest from each other. The internal diameter, d, of the downstream part and the upstream part, respectively, can be about 1.65 metre, and the radius of the bend part at the ends of the downstream part 2 and the upstream part 4 can be 1.5×d.

U-shape and/or nozzle-loop fermentors of the above type are disclosed in DK patent No. 163066 (EP-B-0 418 187). These fermentors are i.a. well suited for use in production processes with methanotrophic bacteria.

Production processes with methanotrophic bacteria are anaerobic and based on natural gas as carbon and energy sources. Atmospheric air, pure oxygen or atmospheric air enriched with pure oxygen is used as oxygenation source in the fermentation process and ammonium is used as nitrogen source. In addition to theses substrates the cultivation of methanotrophic bacteria requires water, phosphate, and several minerals such as magnesium, calcium, potassium, iron, copper, zinc, manganese, nickel, cobalt and molybdenum. Sodium hydroxide and sulphuric acid are used for pH adjustments. All chemicals are food grade. Phosphate is supplied in the form of phosphoric acid, minerals as sulphates, chlorides or nitrates. The pH value is controlled to 6.5±0.3 and the temperature is maintained at 45° C.±2° C.

Methanotrophic bacteria are produced by continuous fermentation. A nozzle-loop fermentor with static mixers is used. The nozzle-loop fermentor brings about high utilization of the gases carried along through the loop with the approximately plug-flowing fermentation liquid, The gases are supplied at the beginning of the loop and stay well admixed with the liquid until their separation off at the headspace at the end of the loop.

Injection in the fermentor can be effected at one or more locations, e.g. at four places—at top, at the middle of the down loop, at the bottom of the down loop, and after the passage of the U-bend part at the bottom a small distance above that. In all circumstances the gases are supplied in advance of the mechanical mixer(s), which is (are) placed immediately after each injection in the flow direction of the fermentor, cf. the figure of the drawing.

Additionally, more mechanical mixers may be placed elsewhere in the fermentor.

The drawback of the prior art U-shape and/or nozzle-U-loop fermentors in connection with the above mentioned production processes with methanotrophic bacteria and corresponding processes, wherein different gases are to be continuously supplied, which partly may be expensive and partly may constitute a potential danger of explosion if they accumulate in major amounts in the reactor, is that up to now it has been difficult or even impossible to supply these gases as well as the additional nutrients (ammonium, phosphate and minerals) necessary for the fermentation process, and pH controlling means in such amounts and relative ratios that it has been possible to obtain an optimum utilization of the gases before the separation off in the headspace of the reactor with simultaneous achievement of an optimally proceeding fermentation process providing the largest possible yield of fermentation product in the shortest possible time. This is due to the fact that hitherto it has been necessary to run the addition of the above mentioned process substances to the reactor on the basis of a predetermined dosage-time schedule which has been worked out on the basis of previously performed test runs during which samples of the fermentation liquid have been taken, which samples subsequently have been analysed for relevant constituent substances in the laboratory. The fermentation processes are, however, biological processes which proceed far from uniformly from time to time, but are subjected to even very large variations for which reason the time-schedule fixed doses will not correspond to the actual need for attainment of the results aimed at with respect to the optimum utilization of the gases before the separation thereof in the headspace of the reactor and attainment of the largest possible yield of fermentation product in the shortest possible time.

SUMMARY OF THE INVENTION

The present invention provides a U-shape and/or nozzle-U-loop fermentor and a method of performing a fermentation process, wherein the above drawbacks are avoided and, thus, it becomes possible to supply necessary gases and the additional nutrients required for the fermentation process, pH adjustment means and water in such amounts and ratios that at all times it corresponds to the actual need for achieving an optimum utilization of the gases before separation thereof in the head-space of the reactor simultaneous with obtaining an optimally proceeding fermentation process with the largest possible yield of fermentation product in the shortest possible period of time.

This object is achieved with the U-shape and/or nozzle-U-loop fermentor according to the invention, which has a U-part consisting of an essentially vertical downstream part 2, an essentially vertical upstream part 4, a U-shape bend part 3 which connects the lower ends of said downstream and upstream parts, an in-line pump 12 placed in the U-part for the circulation of fermentation liquid in the fermentor, a top part 5 placed above the upper end of the downstream part and having the form of a cylinder with a diameter which is substantially larger than the diameter of the downstream part and being connected thereto via a truncated cone-shaped connection member, whereas the upper end of the upstream part 4 via a bend is passed substantially horizontally and tangentially into the lower part of the top part 5, a vent pipe 6 for exhausting the gas(es) separated in the head-space of the top part, an outlet 11, preferably placed in the U-bend part 3, for draining off fermentation liquid, and gas supply means 7,8,9,10, which according to wishes and needs optionally are placed in the downstream part, the U-bend part, and the upstream part, preferably in the lower end thereof, with accompanying static-mechanical mixing members 13,14,15,16,17 for the comminution of the gases introduced into the fermentation liquid, and inlet means for water and nutrient salts 18 and 19, respectively, said fermentor being characterized in that ion sensor(s) or analyser(s) 20,21,22,23 for sensing the concentration of at least one of the ion species phosphate, ammonium, nitrate and hydrogen ion, oxygen sensor(s) for sensing the oxygen concentration and at least one thermo phial for sensing the temperature are provided in-line in the circulating fermentation liquid in connection with the supply means 7,8,9,10,18,19 or in by-pass arrangements attached thereto, said sensor(s), analyser(s) and phial(s) delivering signals to a data processing system (PC) wherein the received signals are processed and the doses of supplied gases, water, minerals and pH controlling means supplied via the supply means 7,8,9,10, 18,19 are calculated and optimised from pre-programmed amounts in relation to the results measured.

From the outlet 11 the fermentation liquid with its content of biomass and dissolved gases, etc. are pumped to a gas separator from which separated residual gases are recirculated to the fermentor, whereas the fermentation liquid is passed to a separator (centrifuge) for up-concentration of the content of solids in the fermentation liquid and from there further on to a sterilization unit and an ultra filtration unit eventually to end up in a spray drying unit, wherein the product solids of the fermentation are recovered, whereas the amounts of liquid separated in these units with their contents of nutrients essentially are recirculated to the fermentor loop.

The invention also relates to a method of performing a fermentation process, by which method water, fermenting micro-organisms, at least two different gases, necessary nutrient salts and pH controlling means as well as possible recovered fermentation liquid (supernatant) are introduced into a U-shape and/or nozzle-U-loop fermentor and fermentation liquid is withdrawn, the fermentation liquid being circulated in the fermentor by means of an in-line pump placed in the U-part of the fermentor, said method being characterized in that the concentration of at least one of the ion species phosphate, ammonium, nitrate and hydrogen ion are sensed by an ion sensor or analyser which is placed in-line in the circulating fermentation liquid in connection with supply means for gases, nutrient salts, pH controlling means and water, in that the oxygen concentration of the fermentation liquid is correspondingly sensed by an oxygen sensor being placed in connection with the respective supply means, and in that the temperature of the fermentation liquid is sensed by at least one thermo phial, the said sensors, analysers and phials delivering signals to a data processing system (PC), wherein the signals received are processed, and the doses of supplied gases, water, minerals and pH controlling means added via the supply means are calculated and optimised from pre-programmed amounts in relation to the results measured.

Preferably, both phosphate, ammonium and nitrate are measured in-line with an ion analyser at the injection of the gases or gas-liquid mixture, and oxygen is also measured in-line with an oxygen sensor. Furthermore, also pH values and temperature are measured in-line.

It is a common feature for all measures and gas injections and other substances of addition that they are controlled and adjusted on the basis of the results measured in the fermentation liquid, which are transferred to a data processing system (PC), wherein the data are processed and the doses of addition via the nozzle arrangements are calculated and optimised from pre-programmed amounts relative to the results measured.

The nozzle arrangement can be a single flow or a multiple flow arrangement. By multiple flows it will be liquid from the fermentor, which is mixed with gas, either oxygen, natural gas or any other gas, before injection under pressure in the fermentor, so that a fine dispersion is obtained.

In case of a multiple flow arrangement ammonium, phosphate and nitrate can be measured via a by-pass in the return flow, e.g. with an ion analyser, and the oxygen content can be measured on-line via other measuring instruments, while other ingredients are monitored via laboratory analyses.

The pressure in the nozzles can be varied so that the dispersion (bubble size) can be measured in the liquid or via a high-speed camera placed in connection with the injection and designed so that switching between the different nozzle arrangements can be effected according to a programmed cycle.

The fermentors are either without pressure or have a constant gauge pressure above that of the atmosphere. The pressure is here controlled via the consumption of the gases injected into the head-space of the fermentor so that a variable counter pressure can be established relative to the residual gases measured in the head-space, and the consumption of the gases is supervised and controlled so that the head-space at no point of time is filled with a mixture of gases which constitutes an explosion risk.

Thus, in operation the fermentor can be without any over pressure in the headspace or with an over pressure of up to 2–3 bars or more.

Similar measurements are performed on the supernatant, which is returned from the centrifugal separation, and on the liquid, which is passed back from ultra filtration, so that back conveyance of these liquids with the contents they may have of different organic and inorganic substances are also incorporated in the optimisation of the fermentor.

No other fermentor, it being a U-nozzle loop or a stirred fermentor, has an optimisation process as that disclosed herein, via on-line measurements, including ion analysers, and optimisation of gas injections and other substance additions via nozzle arrangements, wherein the pressure can be varied relative to the optimum consumption of the gases and security conditions.

BRIEF DESCRIPTION OF THE DRAWINGS

The invention will be further illustrated in more details with reference to FIG. 1 of the drawing, which shows a cross section of an embodiment of a U-shape and/or nozzle-U-Foop fermentor according to the invention with accompanying process auxiliary units and process diagram.

DETAILED DESCRIPTION OF PREFERRED EMBODIMENTS OF THE INVENTION

Figure 1:
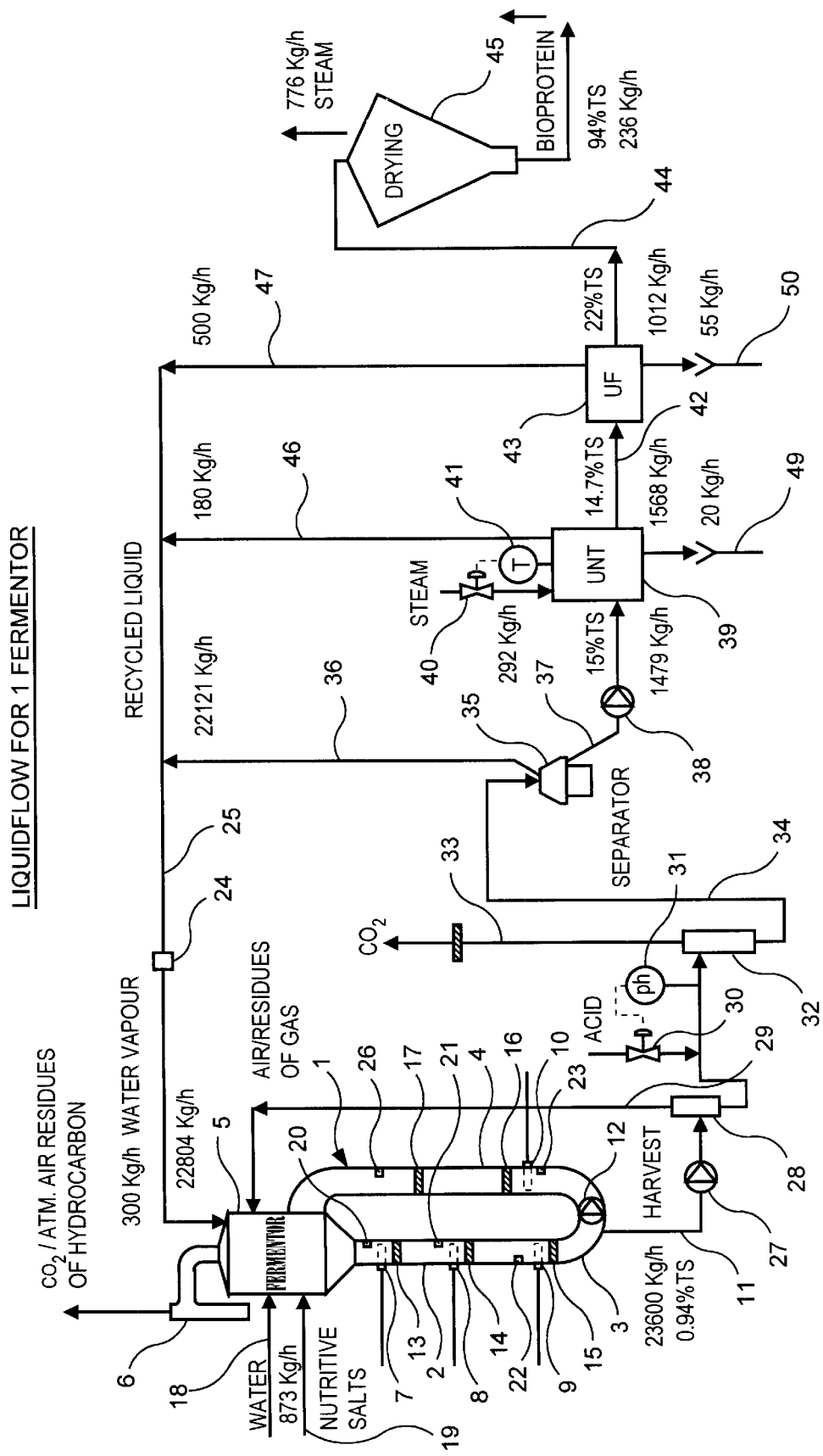

In the FIG. 1 designates the very U-shape and/or nozzle-U-loop fermentor. 2 indicates the downstream part of the fermentor, 3 its U-bend part, and 4 its upstream part. The downstream part 2, the U-bend part 3 and the upstream part 4 constitute together the U-part of the apparatus, which unitarily is denoted 2,3,4. 5 indicates the top part of the fermentor, while 6 indicates a venting tube for exhausting the gas or gases separated in the headspace of the top part. 7 indicates a first member for introducing a gas, e.g. natural gas or methane, 8 indicates another member for introducing the same or another gas, e.g. ammonia and 9 and 10 indicate supply members for the addition of a gas different from the first gas, e.g. atmospheric air, pure oxygen or atmospheric air enriched with pure oxygen. 13,14,15,16 and 17 each indicate a mixing member such as a static-mechanical mixing member for comminution of the preceding supplied gases into numerous small fine bubbles.

18 indicates a supply conduit for water for supplementing the fermentation liquid, 19 indicates a supply conduit for nutrient salts, such as ammonium, magnesium, calcium, potassium, iron, copper, zinc, manganese, nickel, cobalt and molybdenum in the form of sulphates, chlorides oritrates and pH controlling means, and 11 denotes an outlet for draining off fermentation liquid with contents of produced biomass and/or other product substances. Immediately in front of the gas inlet members 7,8,9,10 sensors 20,21,22,23 are provided for sensing the concentrations of the gases in question, e.g. $CH_4$ and $O_2$, and at least one of the ions phosphate, ammonium, nitrate and hydrogen ion. Similar sensors unitarily denoted 24 are provided in the liquid recirculation conduit 25. Besides, a thermo phial 26 for sensing the temperature of the fermentation liquid is provided at at least one location in the fermentor loop. Sensors and phials deliver signals which are conducted to a data processing system (PC) (not shown), wherein they are processed and where the doses of substances supplied via the supply members 7,8,9,10,18,19 are calculated, optimised and controlled from pre-programmed amounts of addition relative to the concentrations measured and calculated.

The fermentation liquid withdrawn through the outlet 11 is pumped by a pump 27 to a gas separator 28, from which the separated air (gases) is passed back to the fermentor, e.g. to the top part 5 thereof, through a conduit 29. Via a dosing nozzle 30 acid, preferably sulphuric acid, is added to the fermentation liquid discharged from the air separator 28, so that a sufficiently low pH is obtained to release $CO_2$. The acid-dosing nozzle 30 is controlled by a signal from the pH sensor 31, which measures the pH value in the fermentation liquid after the addition of acid.

The released $CO_2$ is separated in the $CO_2$ separator 32 and vented from there through a conduit 33 to the atmosphere. The $CO_2$ depleted fermentation liquid is passed through a conduit 34 to a separator 35, such as a centrifuge. In the separator the fermentation liquid is divided into a liquid flow which is substantially depleted for biomass/product substances and which through a conduit 36 is passed back to the fermentor loop through the recirculation conduit 25, and another liquid flow which is enriched with biomass/product substances and which through a conduit 37 is pumped by the pump 38 to a sterilization unit 39 (UHT=Ultra High Temperature). The sterilization unit is supplied superheated steam through the steam supply nozzle 40 which is controlled by a signal from the temperature phial 41 (T), so that the concentrated fermentation liquid attains a temperature of e.g. 140° C.

The sterilized fermentation liquid is quenched to e.g. 70° C. and is passed through a conduit 42 to an ultra filtration unit 43 (UF), wherein a further concentration of biomass/product substances occurs, which through a conduit 44 is conducted to a spray-drier 45, wherein the major part of the residual liquid is removed and biomass/product substances having a content of solids of e.g. about 94% are withdrawn.

From the sterilization unit 39 and the ultra filtration unit 43 liquid flows having a low content of biomass/product substances are drained off through conduits 46 and 47, respectively, which conduct these liquid flows back to the fermentor loop via the recirculation conduit 25.

From the sterilization unit 39 and the ultra filtration unit 43 small flows of condensates are further withdrawn, which are collected via the collection conduits 49 and 50, respectively.

Example of Production

As an example of the application of the fermentor described above with accompanying process auxiliary units, a production of single cell protein using natural gas as carbon and energy sources will be described in the following.

Initially, the fermentation system is cleaned with hot sodium hydroxide followed by a short treatment with dilute nitric acid solution and sterilization with super heated steam having a temperature of 120° C. for one hour. The fermentor is then filled with water, which has been heat-sterilized at 130° C. for 10 seconds. Gases and solutions of minerals, ammonia and phosphoric acid are also sterilized before they are fed into the fermentor.

Atmospheric air, pure oxygen or atmospheric air enriched with pure oxygen is used as oxygen source and ammonia is used as nitrogen-source. Additionally, phosphate is introduced as phosphoric acid and minerals, such as magnesium, calcium, potassium, iron, copper, zinc, manganese, nickel, cobalt and molybdenum, in the form of sulphate, chloride or nitrate salts. Besides, sodium hydroxide and sulphuric acid are supplied for controlling the pH of the fermentation liquid so that it is at 6.5±0.3, while the temperature is maintained at 45° C.±2° C.

*Methylococcus capsulatus* (*M. capsulatus*) is used as methanotrophic microorganism for the utilization of the supplied gases. *M. capsulatus* metabolises the methane in the natural gas into biomass and carbon dioxide. However, natural gas frequently contains 5–10% ethane and higher hydrocarbons, and *M. capsulatus* can only oxidize these hydrocarbons into the corresponding alcohols, aldehydes and carboxylic acids, but cannot oxidize these completely to solely carbon dioxide and water or utilize them for biomass production. Therefore, a pure culture of *M. capsulatus*, which is supplied with natural gas, will accumulate acetic acid and other carboxylic acids due to the content of higher hydrocarbons in the natural gas. Accumulated high concentrations of carboxylic acids inhibit the growth of *M. capsulatus* and, therefore, the fermentation liquid is supplemented with three heterotrophic bacteria, which are selected so that a fermentation ecosystem is obtained, in which all product niches are occupied. Their main function is to exploit acetic acid and other carboxylic acids and degrade them to carbon dioxide so that carboxylic acid accumulation is avoided.

When the entire U-shape fermentor has been filled with water and the necessary nutrient salts and an inoculation culture of microorganisms have been added, the fermentation liquid circulation is started and propelled by the in-line pump 12, whereupon the feed gases natural gas, ammonia and oxygen (atmospheric air) are introduced into the fermentation liquid until a steady state with a biomass content of 2–3% solids is obtained. Then withdrawing of fermentation liquid through the outlet 11 is initiated simultaneously with supplying water and recirculation liquid (supernatant) at a dilution rate of 0.20–0.25 $h^{-1}$. From then, the supply of gases, nutrient salts and pH adjustment means is effected on the basis of in-line measurements of ammonium, phosphate and nitrate as well as oxygen and methane by the sensors 20–23 in the fermentor loop and by the sensors 24 in the conduit 25 for recirculation liquid (supernatant). Besides, determinations of the headspace gases can be performed in the top part 5 of the fermentor. The calculations for addition of gases and nutrient salts are performed in the data processing system (PC) (not shown in FIG. 1) on the basis of the measurement signals delivered from the sensors and a detailed knowledge about the stoichiometric demands of the different minerals for the fermentation culture used.

When the whole fermentation plant with appending process auxiliary units have reached the stationary condition, at which the biomass content in the fermentation liquid is about 2–3% solids, the supply process and product flows are e.g. as shown in FIG. 1 of the drawing. This state of production with continuous operation can subsequently be maintained for 4–5 weeks, whereupon the plant is emptied, cleaned and restarted as described above.

The fermentation liquid with a biomass content of 2–3% solids withdrawn from the U-loop fermentor is concentrated in the separator 35 to a contents of solids of about 15%, is quickly heated in the sterilization unit 39 to a temperature of about 140° C. for the attainment of a sterile product, and is then quenched to about 70° C. Hereby the biomass is inactivated and the cells undergo lyses so that the protein becomes more accessible. Finally, the sterilized biomass is dried in the spray drier unit 45 having an integrated fluidised bed. Hereby a non-dusty agglomerated product having a content of solids (TS) of e.g. 94% by weight is obtained.

In order to minimise the consumption of process water and to minimise the amount of wastewater, the process water (supernatant) separated by the separator 35, by the sterilization unit 39 and by the ultra filtration unit 43 is returned after a short heat treatment.

The product obtained is routinely examined for microbial contaminations, water content and chemical composition. Tests have shown that the sterilization treatment kills all the fermentation bacteria used in the production.

The spray drying is the last step in the production of the biomass protein, which does not undergo further processing before final use.

The protein product obtained is a free-flowing, reddish-brown, non-dusty agglomerate with a particle size of 150–200 μm.

Analyses of the biomass protein product have on a dry weight basis given the following average composition values:

| Composition | Weight % |
|---|---|
| Crude protein | 70.6 |
| Crude fat | 9.8 |
| Ash | 7.1 |
| Crude fibre | 0.7 |
| N-free extract | 11.8 |
| Total | 100.0 |

What is claimed is:

1. A U-shape and/or nozzle-U-loop fermentor having a U-part consisting of an essentially vertical downstream part (2), an essentially vertical upstream part (4), a U-shape bend part (3), which connects the lower ends of the downstream and the upstream parts, an in-line pump (12) placed in the U-part for circulation of fermentation liquid in the fermentor, a top part (5) which is provided above the upper end of the downstream part and has the form of a cylinder with a diameter which is substantially larger than the diameter of the downstream part and is connected thereto via a truncated cone-shaped connection part, the upper end of the upstream part (4) being passed essentially horizontally and tangentially into the lower part of the top part (5) via a bend, a vent tube (6) for discharging gas(es) released in the headspace of the top part, an outlet (11) preferably placed in the U-bend part (3) for withdrawing fermentation liquid, and gas supply members (7,8,9,10) which according to wishes and demand optionally are placed in the downstream part, the U-part and the upstream part, preferably in the lower end thereof, with accompanying static-mechanical mixing members (13,14,15,16,17) for comminution of the gases introduced into the fermentation liquid, and inlet members for water and nutrient salts (18) and (19), respectively, comprising in that one (or more) ion sensor(s) or analyser(s) (20,21,22,23) for sensing the concentration of at least one of the ion species phosphate, ammonium, nitrate and hydrogen ion, oxygen sensor(s) for sensing the oxygen concentration, and at least one thermo phial for sensing the temperature are provided in-line in the circulating fermentation liquid in connection with the supply members (7,8,9,10,18,19) or in by-pass arrangements in connection therewith, said sensor (s), analyser(s) and phial(s) deliver signals to a data processing system, and that sensors (24) are also provided in a recirculation conduit (25) for sensing the concentration of at least one of the ion species phosphate, ammonium, nitrate and hydrogen ion, said sensors also deliver signals to the data processing system, wherein the signals received are processed and the dosage of feed gases, water, minerals and pH adjustment means via the supply members (7,8,9,10,18, 19) are calculated and optimised from pre-programmed amounts relative to the results measured.

2. A fermentor according to claim 1, further comprising in that at least one of the sensors (20,21,22,23), is capable of sensing the concentration of methane in the fermentation liquid and deliver a corresponding signal to the data processing system, wherein it is processed and included in the calculation and optimisation of the dosage of feed gases, water, minerals and pH adjustment means via the supply members (7,8,9,10,18,19) from pre-programmed amounts relative to the results measured.

3. A fermentor according to claim 1, further comprising in that the sensors or analysers (20,21,22,23,24) are capable of sensing the concentration of all the ion species phosphate, ammonium, nitrate and hydrogen ion, and the oxygen concentration and delivering signals to the data processing system, wherein the signals received are processed and the dosage of feed gases water, minerals and pH adjustment means via the supply members (7,8,9,10,18,19) are calculated and optimised from pre-programmed amounts relative to the results measured.

4. A method of effecting a fermentation process, by which method water, fermenting microorganisms, at least two different gases, necessary nutrient salts and pH adjustment means as well as any recovered fermentation liquid (supernatant) are introduced into a U-shape and/or nozzle-U-loop fermentor and fermentation liquid is withdrawn, the fermentation liquid being circulated in the fermentor by means of an in-line pump provided in the U-part of the fermentor, comprising the concentration of at least one of the ion species phosphate, ammonium, nitrate and hydrogen ion is sensed with an ion sensor or analyser placed in-line in the circulating fermentation liquid in connection with the supply members for gases, nutrient salts, pH adjustment means and water, that the oxygen concentration in the fermentation liquid correspondingly is sensed with an oxygen sensor placed in connection with the respective supply member, and the temperature of the fermentation liquid is sensed with at least one thermo phial, the said sensors, analysers and phials delivering signals to a data processing system, and that the concentration of at least one of the ion species phosphate, ammonium, nitrate and hydrogen ion, is sensed with sensor(s) provided in a recirculation conduit, said sensor(s) also delivering signals to the data processing system, wherein the signals received are processed and the dosage of feed gases, water, minerals and pH adjustment means via the supply members are calculated and optimised from pre-programmed amounts relative to the results measured.

5. A method according to claim 4, further comprising in that the concentration of all the ion species phosphate, ammonium, nitrate and hydrogen ion are sensed with ion sensors or analysers placed in-line in the circulating fermentation liquid in connection with the supply members for gases, nutrient salts, pH adjustment means and water, and that the sensors or analysers deliver signals to a data processing system, wherein the signals received are processed and the dosage of feed gases, water, minerals and pH adjustment means via the supply members are calculated and optimised from pre-programmed amounts relative to the results measured.

6. A method according to claim 4 further comprising that the fermentation process is a methanotrophic fermentation process and at least one of the gases introduced into the fermentation liquid is methane or natural gas and that additionally one gas is introduced, which is either atmospheric air, pure oxygen or atmospheric air enriched with oxygen.

7. A method according to claim 6, further comprising that additionally ammonia is introduced into the fermentation circulation loop as nitrogen source for the fermentation process.

8. A method according to claim 7, further comprising that methane or natural gas, ammonia, and atmospheric air, pure oxygen or atmospheric air enriched with oxygen are introduced in the said order in the flow direction of the fermentation liquid in the U-loop fermentor as viewed from the upper end of the downstream part of the fermentor.

9. A method according to claim 6, further comprising that also the concentration of methane in the fermentation liquid is sensed with a sensor or analyzer which deliver a corresponding signal to the data processing system, wherein the signal is processed and included in the calculation and optimisation of the dosage of feed gases, water, minerals and pH adjustment means via the supply members (7,8,9,10,18, 19) from pre-programmed amounts relative to results measured.

* * * * *